United States Patent [19]
Nagano et al.

[11] Patent Number: 5,874,590
[45] Date of Patent: Feb. 23, 1999

[54] DIAMINOFLUORESCEIN DERIVATIVE

[75] Inventors: Tetsuo Nagano, 32-25-110, Asagaya-kita 3-chome, Suginami-ku, Tokyo 166; Hirotatsu Kojima, Tokyo, both of Japan

[73] Assignee: Tetsuo Nagano, Tokyo, Japan

[21] Appl. No.: 953,724

[22] Filed: Oct. 17, 1997

[30] Foreign Application Priority Data

Feb. 19, 1997 [JP] Japan ................................ 9-034547

[51] Int. Cl.$^6$ ............... C07D 311/82; C07D 487/00; G01N 21/76
[52] U.S. Cl. ............. 549/223; 548/256; 436/172; 252/301.19; 252/301.21
[58] Field of Search ............. 549/223; 436/172; 548/256; 252/301.19, 301.21

[56] References Cited

U.S. PATENT DOCUMENTS 4,321,057  3/1982  Buckles ........................................ 435/7
5,686,310  11/1997  Haystead et al. ........................ 436/172

FOREIGN PATENT DOCUMENTS 9-43153  2/1997  Japan .

OTHER PUBLICATIONS

16th Symposium on Medicinal Chemistry 5th Annual Meeting of Division of Medicinal Chemistry–The Pharmaceutical Society of Japan Division of Medicinal Chemstry––Toyama, Nov. 27–29, 1996, entitled: "Development of fluorecent indicators for bioimaging of nitric oxide", at pp. 165–166, published Oct. 23, 1996.

Kojima et al 'Development of a fluorescent indicator for nitric oxide based on fluorescein chromophere' CA 128: 254765, 1998.

Maeda et al., Journal of Leukocyte Biology, 56, pp. 588–592, 1994.

Akaike et al., Biochemistry, 32, pp. 827–832, 1993.

Organic Chemicals Catalog, 32, p. 1229, 1994, Tokyo Kasei Co., Ltd.

Hrabie, J. Org. Chem., 58, pp. 1472–1476, 1993.

Kikuchi et al., Biol. Pharm. Bill., 19, pp. 649–651, 1996.

Gendai Kagaku (Chemistry Today), pp. 25–29, Apr. 1994.

Palmer et al., Nature, 327, pp. 524–526, 1987.

Kelm et al., Circulation Research, 66, No. 6, pp. 1561–1575, 1990.

Shibuki, Neroscience Research, 9, pp. 69–76, 1990.

Malinski et al., Nature, 356, pp. 676–678, 1992.

Green et al., Analytical Biochemistry, 126, pp. 131–138, 1982.

"3 Method for the Measurement of NO," by Tetsuo Nagano, pp. 42–52.

"Approach from the Latest Medicine 12, NO," edited by Noboru Toda, published by Medical View Co., Ltd., pp. 42–52.

Archer, FASEB Journal, 7, 349–360, 1993.

Stainton, Analytical Chemistry, 46, No. 11, p. 1616, 1974.

Sawicki et al., Microchemical Journal, 16, pp. 657–672, 1971.

Wiersma, Analytical Letters, 3, No. 3, pp. 123–132, 1970.

Sawicki, Analytical Letters, 4, No. 11, pp. 761–775, 1971.

Damiani et al., Talanta, 33, No. 8, pp. 649–652, 1986.

Misko et al., Analytical Biochemistry, 214, pp. 11–16, 1993.

DOIJN News, No. 74, Information, "A Reagent for the Determination of NO; 2,3–diaminonaphthalene," Dojindo Laboratories Inc., 1995.

*Primary Examiner*—Amelia Owens
*Attorney, Agent, or Firm*—Greenblum & Bernstein, P.L.C.

[57] ABSTRACT

A compound useful for the measurement of nitrogen monoxide under a substantially neutral condition which is represented by the following formula (I):

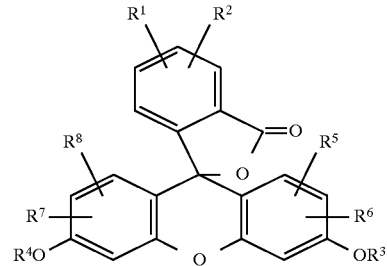

wherein $R^1$ and $R^2$ represent amino groups that substitute at adjacent positions on the phenyl ring; $R^3$ and $R^4$ independently represent a hydrogen atom or an acyl group; $R^5$, $R^6$, $R^7$, and $R^8$ independently represent a hydrogen atom, a $C_{1-6}$ alkyl group, allyl group, or a halogen atom.

11 Claims, 5 Drawing Sheets

DIAMINOFLUORESCEIN DERIVATIVE

BACKGROUND OF THE INVENTION

1. Field of the Invention

The present invention relates to fluorescein derivatives which are useful for reagents for measurement of nitrogen monoxide. It also relates to reagents for measuring nitrogen monoxide which comprise said compounds.

2. Related Art

Nitrogen monoxide (NO) is an unstable radical having a short life, and it has been elucidated that nitrogen monoxide has important functions as a physiologically active substance in a living body (featured in Gendai Kagaku (Chemistry Today), April, 1994). Methods for measuring nitrogen monoxide are mainly classified into (a) indirect methods where oxidative degradation products of nitrogen monoxide such as $NO_2$— or $NO_3$— are measured, and (b) methods where nitrogen monoxide is directly measured. The direct methods have been focused from the standpoint that they achieve detection and quantification of nitrogen monoxide under physiological condition. However, no measuring method has been developed to date that has sufficient specificity and high sensitivity and is applicable to an in vitro system.

For example, a chemiluminescence method which utilizes luminescence emitted during an ozonic oxidation of NO radicals (Palmer, R. M., et al., Nature, 327, pp.524–526, 1987); a method which comprises the step of measuring an absorption spectrum of metHb that is produced by an oxidation of oxyhemoglobin ($O_2Hb$) (Kelm, M., et al., Circ. Res.66, pp.1561–1575, 1990); a method which comprises the step of measuring electric current generated during an oxidation by means of electrodes that are inserted into a tissue (Shibuki, K., Neurosci. Res.9, pp.69–76, 1990; Malinski, T., Nature, 356, pp.676–678, 1992); and the Griess reaction method (Green, L. C., et al., Anal. Biochem., 126, pp.131–138, 1992) are known as typical methods (as reviews, see, "3. Method for the measurement of NO," by Tetsuo Nagano, pp.42–52, "Approach from the Latest Medicine 12, NO" edited by Noboru Toda, published by Medical View Co., Ltd.; and Archer, S., FASEB J., 7, pp.349–360, 1993).

The Griess reaction method comprises a detection step that utilizes the azo coupling between naphthylethylenediamine and a diazonium salt compound formed with $NO_2$— which is generated by the oxidation of nitrogen monoxide radicals. This method is advantageous because it does not require particular apparatuses or techniques, although nitrogen monoxide radicals are not directly measured in this method. In addition, $NO_3$— can also be measured after being reduced to $NO_2$— by using cadmium (Stainton, M. P., Anal. Chem., 46, p.1616, 1974; Green, L. C., et al., Anal. Biochem., 126, pp.131–138, 1982) or hydrazine (Sawicki, C. R. and Scaringelli, F. P., Microchem. J., 16, pp.657–672, 1971), and accordingly, the method also has characteristic feature that it enables the measurement of metabolites related to nitrogen monoxide.

2,3-Diaminonaphthalene has also been known as a reagent for measuring nitrogen monoxide by detecting $NO_2$—, as in a similar manner to Griess reaction method. This reagent reacts with $NO_2$— under an acidic condition to form a fluorescent adduct, i.e., naphthalenetriazole (chemical name: 1-[H]-naphtho[2,3-d]triazole) (Wiersma, J. H., Anal. Lett., 3, pp.123–132, 1970). The reaction conditions of 2,3-diaminonaphthalene and $NO_2$— have been detailedly studied, and it has been found that the reaction proceeds most rapidly at a pH not higher than 2, and completes within about 5 minutes at room temperature (Wiersma, J. H., Anal. Lett., 3, pp.123–132, 1970; Sawicki, C. R., Anal. Lett., 4, pp.761–775, 1971). The resulting adduct emits fluorescence most efficiently at a pH not lower than 10 (Damiani, P. and Burini, G., Talanta, 8, pp.649–652, 1986).

The method for measuring nitrogen monoxide by using the above 2,3-diaminonaphthalene has characteristic features of 50- to 100-fold higher sensitivity compared to the Griess reaction method and of detection limit at approximately several tens nM (Misko, T. P., Anal. Biochem. 214, pp.11–16, 1993). This method is highly advantageous because it does not need particular apparatuses or techniques and can be conveniently carried out (as a review of the aforementioned method, see, DOJIN News. No. 74, Information, "A reagent for the determination of NO: 2,3-diaminonaphthalene," Dojindo Laboratories Inc., 1995). However, this method does not utilize nitrogen monoxide, per se, but it utilizes an oxidation product, i.e., $NO_2$—, as a reactant. Accordingly, the method is considered as an indirect method when compared to those including direct measurement of nitrogen monoxide. Furthermore, because the reaction of 2,3-diaminonaphthalene with $NO_2$— is progressed under a strongly acidic condition (pH not higher than 2), the method has a problem in that it cannot be employed for detection or quantification of nitrogen monoxide under a physiological condition.

The inventors of the present invention conducted researches to provide a means that enables direct and highly sensitive measurement of nitrogen monoxide under a physiological condition, and as a result, they found that nitrogen monoxide can efficiently react with 2,3-diaminonaphthalene or its derivatives, even under a neutral condition, in the presence of an oxygen source such as dissolved oxygen or oxide compounds (e.g., PTIO and derivatives thereof such as carboxy-PTIO), and a fluorescent naphthalenetriazole or a derivative thereof is obtained. They also found that a method for measuring nitrogen monoxide utilizing the above reaction has extremely high detection sensitivity, and can achieve accurate quantification of very small amount of nitrogen monoxide (see, the specification of Japanese Patent Application No. Hei 7-189978).

However, the aforementioned method utilizing 2,3-diaminonaphthalene requires the irradiation with excitation light having a short wavelength of approximately 370–390 nm for the detection of fluorescence, and this may cause damages to cells and/or tissues in a measurement system. Strong autofluorescence of cells, per se, may also possibly affect this measurement, and moreover, there is a problem that a fluorescence filter provided on a usual fluorescence microscope fails to sufficiently cut off excitation light during fluorescence measurement. In addition, the fluorescent triazole compound formed from the 2,3-diaminonaphthalene has rather insufficient fluorescence intensity, and therefore, it is difficult to achieve accurate measurement of intracellular fluorescence of an individual cell by ordinary fluorescence microscopy. Since 2,3-diaminonaphthalene itself has a simple chemical structure, there is also a problem that the compound is not suitable as a fundamental structure for various chemical modifications to achieve intracellular localization of a reagent.

SUMMARY OF THE INVENTION

An object of the present invention is to provide compounds which are useful for measurement of nitrogen mon- oxide. More specifically, the object of the present invention is to provide compounds which can efficiently react with nitrogen monoxide under a neutral condition and provide a fluorescent substance having excellent fluorescence intensity.

Another object of the present invention is to provide a compound which has the aforementioned characteristic features and enables the measurement of nitrogen monoxide by means of excitation light having a long wavelength which does not cause damages to living tissues and cells.

A further object of the present invention is to provide a reagent for measuring nitrogen monoxide which comprises a compound having the aforementioned characteristic features. More specifically, the object is to provide a reagent for measuring nitrogen monoxide which enables accurate measurement of nitrogen monoxide of an individual cell that exists inside the cell.

The inventors of the present invention made diligent efforts to achieve the foregoing objects, and as a result, they found that a particular class of fluorescein derivatives, which themselves emit almost no fluorescence, can easily react with nitrogen monoxide under a neutral condition, and give triazole compounds having high fluorescence intensity. They also found that the triazole derivatives can emit strong fluorescence at approximately 515 nm when irradiated with excitation light having a longer wavelength of around 495 nm, and the excitation light can be easily cut off by means of a fluorescence filter provided on an ordinary fluorescence microscope. They further found that intracellular nitrogen monoxide concentration can be conveniently measured by measuring fluorescence of the individual cells. The present invention was achieved on the basis of these findings.

The present invention thus provides a compound represented by the following formula (I):

wherein $R^1$ and $R^2$ represent amino groups that substitute at adjacent positions on the phenyl ring; $R^3$ and $R^4$ independently represent a hydrogen atom or an acyl group; $R^5$, $R^6$, $R^7$, and $R^8$ independently represent a hydrogen atom, a $C_{1-6}$ alkyl group, allyl group, or a halogen atom. According to a preferred embodiment of the present invention, there is provided a compound of the above formula wherein $R^3$ and $R^4$ independently represent a hydrogen atom or a $C_{1-6}$ alkylcarbonyl group; and $R^5$, $R^6$, $R^7$, and $R^8$ independently represents a hydrogen atom or a chlorine atom. According to another embodiment of the present invention, there is provided a reagent for measurement of nitrogen monoxide which comprises the aforementioned compound.

According to another aspect of the present invention, there is provided a compound represented by the following formula (II):

wherein $R^{11}$ and $R^{12}$ combine together to form a group represented by —N=N—$NR^{19}$— which forms a ring structure at adjacent positions on the phenyl ring wherein $R^{19}$ represents a hydrogen atom, a $C_{1-18}$ alkyl group, or a substituted or unsubstituted aralkyl group, or $R^{11}$ and $R^{12}$ represent a combination of an amino group and a nitro group which substitute at adjacent positions on the phenyl ring; $R^{13}$ and $R^{14}$ independently represent a hydrogen atom or an acyl group; and $R^{15}$, $R^{16}$, $R^{17}$, and $R^{18}$ independently represent a hydrogen atom, a $C_{1-6}$ alkyl group, allyl group, or a halogen atom. According to a preferred embodiment of the above aspect of the present invention, there is provided the compounds of the formula (II) wherein $R^{13}$ and $R^{14}$ independently represents a hydrogen atom or a $C_{1-6}$ alkylcarbonyl group; and $R^{15}$, $R^{16}$, $R^{17}$, and $R^{18}$ independently represent a hydrogen atom or a chlorine atom.

According to a further aspect of the present invention, there is provided a method for measuring nitrogen monoxide which comprises the steps of (1) reacting a compound represented by the above formula (I) with nitrogen monoxide; and (2) detecting a compound of the formula (II) formed by the above step (1).

BRIEF DESCRIPTION OF THE DRAWINGS

show the results of successive experiments. FIG. (a) shows the fluorescent changes after the culture medium of the stimulated cells was replaced with a culture medium containing 1 mM L-Arg; FIG. (b) shows the changes after the culture medium of the step (a) was replaced with a culture medium containing 1 mM NMMA; and FIG. (c) shows the changes after the culture medium of the step (b) was replaced with a culture medium containing 10 mM L-Arg. FIG. (d) shows the changes after the culture medium of the stimulated cells was replaced with a culture medium containing 1 mM NMMA. FIG. (e) shows the changes after the culture medium of the non-stimulated cells was replaced with a culture medium containing 1 mM L-Arg. The normal lines represent fluorescence intensities of individual cells, and the bold lines represent average values.

PREFERRED EMBODIMENTS OF THE INVENTION

In the above general formula (I), $R^1$ and $R^2$ represent amino groups which substitute at adjacent positions on the phenyl ring. Both of $R^1$ and $R^2$ may preferably be unsubstituted amino groups, or either of $R^1$ and $R^2$ may be a monosubstituted amino group. As the substituent of the amino group, examples include a straight- or branched-chain $C_{1-6}$ alkyl group (preferably a $C_{1-6}$ alkyl group), a $C_{1-6}$ alkyl group substituted with an unsubstituted or substituted aryl group (i.e., aralkyl group) or the like. In the specification, the $C_{1-6}$ alkyl group embraces both of either straight- or branched-chain groups unless specifically mentioned, and more specifically, methyl group, ethyl group, n-propyl group, isopropyl group, n-butyl group, sec-butyl group, tert-butyl group and the like may be used. As the aryl-substituted alkyl group, for example, benzyl group, phenethyl group, p-methoxybenzyl group, p-ethoxycarbonylbenzyl group, p-carboxybenzyl group and the like may be used.

$R^3$ and $R^4$ independently represent a hydrogen atom or an acyl group. Examples of the acyl group include, for example, an arylcarbonyl group such as benzoyl group, p-methoxybenzoyl group, p-chlorobenzoyl group, or naphthylcarbonyl group; a $C_{1-6}$ alkylcarbonyl group such as acetyl group, propionyl group, or butanoyl group or other. $R^3$ and $R^4$ may independently be a hydrogen atom or an acetyl group, and most preferably, both of $R^3$ and $R^4$ are hydrogen atoms or both are acetyl groups.

$R^5$, $R^6$, $R^7$ and $R^8$ independently represent a hydrogen atom, a $C_{1-6}$ alkyl group, allyl group ($CH_2=CH-CH_2-$), or a halogen atom. The halogen atom may be any one of a fluorine atom, a chlorine atom, a bromine atom, or an iodine atom, and a chlorine atom may preferably be used. It is preferred that $R^5$, $R^6$, $R^7$, and $R^8$ independently represent a hydrogen atom or a chlorine atom. More preferably, both of $R^5$ and $R^6$ are hydrogen atoms or chlorine atoms, and both of $R^7$ and $R^8$ are hydrogen atoms. Although substituting positions of $R^5$ and $R^6$ as well as $R^7$ and $R^8$ on the phenyl ring are not particularly limited, it is preferred that they substitute at positions selected from 2-, 4-, 5-, and 7-positions of the xanthene structure.

In the aforementioned formula (II), $R^{11}$ and $R^{12}$ combine together to represent the group $-N=N-NR^{19}-$ which forms a ring structure at adjacent positions on the phenyl ring. $R^{19}$ represents a hydrogen atom, a straight- or branched-chain $C_{1-18}$ alkyl group (preferably a $C_{1-6}$ alkyl group) or a $C_{1-6}$ alkyl group substituted with an unsubstituted or substituted aryl group. As the aryl-substituted alkyl group, for example, benzyl group, phenethyl group, p-methoxybenzyl group, p-ethoxycarbonylbenzyl group, p-carboxy-benzyl group and the like may be used. $R^{11}$ and $R^{12}$ also represent a combination of an amino group and a nitro group which substitute at adjacent positions on the phenyl ring, wherein one of $R^{11}$ and $R^{12}$ represents an amino group and the other represents a nitro group. The amino group represented by $R^{11}$ or $R^{12}$ may be unsubstituted, or may have one substituent such as, for example, a $C_{1-}$alkyl group (preferably a $C_{1-6}$ alkyl group), a $C_{1-6}$ alkyl group substituted with a substituted or unsubstituted aryl group as explained above. The amino group may have an acyl group such as acetyl group, trifluoroacetyl group, or benzoyl group, or a protective group such as alkylsilyl groups including trimethylsilyl group. An arylalkyl group such as benzyl group may also be used as the protective group.

$R^{13}$ and $R^{14}$ independently represent a hydrogen atom or an acyl group. As the acyl group, for example, an arylcarbonyl group such as benzoyl group, p-methoxybenzoyl group, p-chlorobenzoyl group, or naphthylcarbonyl group; a $C_{1-6}$ alkylcarbonyl group such as acetyl group, propionyl group, or butanoyl group or other may be used. Preferably, $R^{13}$ and $R^{14}$ independently represent a hydrogen atom or acetyl group, and most preferably, both of $R^{13}$ and $R^{14}$ are hydrogen atoms or acetyl groups.

$R^{15}$, $R^{16}$, $R^{17}$, and $R^{18}$ independently represent a hydrogen atom, a $C_{1-6}$ alkyl group, allyl group, or a halogen atom. The halogen atom may be any one of a fluorine atom, a chlorine atom, a bromine atom, or an iodine atom, and may preferably a chlorine atom. It is preferred that $R^{15}$, $R^{16}$, $R^{17}$, and $R^{18}$ independently represent a hydrogen atom or a chlorine atom, and it is further preferred that both of $R^{15}$ and $R^{16}$ are hydrogen atoms or chlorine atoms, and both of $R^{17}$ and $R^{18}$ are hydrogen atoms. Although substituting positions of $R^{15}$ and $R^{16}$ as well as $R^{17}$ and $R^{18}$ on the phenyl ring are not particularly limited, it is preferred that they substitute at positions selected from 2-, 4-, 5-, and 7-positions of the xanthene structure.

The compounds of the formula (I) and the formula (II) wherein $R^{11}$ and $R^{12}$ represent the combination of an amino group and a nitro group substituting at adjacent positions on the phenyl ring can be prepared, for example, according to the schemes set out below. The details of the methods will be specifically explained in the example section of the specification. It will be understood that the compounds of the formula (II) are useful as synthetic intermediate compounds for the preparation of the compounds of the formula (I). Among the compounds represented by the formula (II), those wherein $R^{11}$ and $R^{12}$ combine together to represent the group $-N=N-NR^{19}-$ that forms a ring structure at adjacent positions on the phenyl ring can be prepared by reacting the compounds of the aforementioned formula (I) with nitrogen monoxide. These compounds are highly fluorescent as explained later, and are useful for the measurement of nitrogen monoxide.

By referring to the general explanations in the above schemes and specific explanations in the examples, one of ordinarily skilled artisan will readily understand that the compounds embraced by the formula (I) and the formula (II) can easily be prepared. Methods for preparing fluorescein derivatives having various kinds of substituents are known, and therefore, those skilled in the art can readily prepare any compounds that fall within the formula (I) and (II) by combining known methods available to skilled artisan with the methods disclosed in the examples of the specification. The compounds of the formula (I) and the formula (II) according to the present invention may have one or more asymmetric carbon atoms. Any optical isomers of the compounds based on one or more asymmetric carbon atoms which are optically pure forms, any mixtures of the optical isomers, racemates, diastereoisomers in pure forms, mixtures of the diastereoisomers and other fall within the scope of the present invention. The compounds of the formula (I) and the formula (II) of the present invention may exist as base addition salts such as sodium salts or potassium salts, or acid addition salts such as hydrochlorides, sulfates, or p-toluenesulfonates. Any one of these salts also falls within the scope of the present invention. Furthermore, the compounds of the present invention in free forms or in the forms of the salt may exist as hydrates or solvates, and it should be understood that they also fall within the scope of the present invention.

Fluorescein derivatives are also known to exist as compounds without forming a lactone ring, i.e., 9-(o-carboxyphenyl)-6-hydroxy-3H-xanthen-3-one derivatives. The compounds of the present invention may also exist in the form of the aforementioned structural isomer, and it will be readily understood by those skilled in the art that they also fall within the scope of the present invention. In the formulas (I) and (II), and in the schemes set out above, only the compounds having a lactone ring are shown from a viewpoint of simplicity.

The compounds represented by the formula (I) of the present invention have characteristic property that they efficiently react with nitrogen monoxide under a neutral condition and provide compounds of the formula (II) wherein $R^{11}$ and $R^{12}$ combine together to form the group —N=N—NR$^{19}$— which forms a ring structure at adjacent positions on the phenyl ring. The compounds represented by the formula (I), per se, emit almost no fluorescence when irradiated with excitation light of 495 nm under a neutral condition, whereas the compounds of the above formula (II) have the property of emitting extremely strong fluorescence (emission: 515 nm) under the same condition. Therefore, nitrogen monoxide in a living tissues or a cell can be measured by introducing the compound represented by the formula (I) into a living tissue or a cell to allow the compound react with nitrogen monoxide to form the fluorescent compound of the above formula (II), and measuring the fluorescence of said compound.

The method for measurement of nitrogen monoxide provided by the present invention comprises the steps of allowing a compound represented by the above formula (I) react with nitrogen monoxide to form a compound of formula (II), and measuring fluorescence of the compound of the formula (II). The term "measurement" used in the specification should be construed in its broadest sense, which includes various measurement purposes such as, for example, detection, quantification, qualitative analysis and other. The above reaction can preferably be carried out under a neutral condition, for example, in the range of from pH 6.0 to 8.0, preferably in the range of from pH 6.5 to 7.8, and more preferably in the range of from pH 6.8 to 7.6. However, the measurement of nitrogen monoxide according to the present invention is not limited to those under the neutral range. For example, the measurement can also be performed under a strongly acidic condition such as in gastric mucosal cells.

Among the compounds of the formula (I), those wherein $R^5$ and $R^6$ are chlorine atoms can advantageously maintain sensitivity approximately in the pH range of from 5 to 8, and therefore, where measurement under a wide range of pH is required, these compounds may preferably be used as reagents. In addition, the compounds wherein $R^3$ and $R^4$ are acetyl groups can easily pass through a cellular membrane so as to be taken into the inside of a cell, and then they are converted into the compounds wherein $R^3$ and $R^4$ are hydrogen atoms after the hydrolysis of the ester of the acetoxy groups. The resulting dihydroxy compound are highly hydrophilic, and not easily excreted from the intracellular environment. Accordingly, the compound wherein $R^3$ and $R^4$ are acetyl groups are useful as a reagent for measurement, per se, but useful as a so-called pro-drug for intracellularly transporting the reagent (the compound wherein $R^3$ and $R^4$ are hydrogen atoms) at a high concentration.

The measurement of fluorescence can be carried out according to a known fluorometry method (see, for example, Wiersma, J. H., Anal. Lett., 3, pp.123–132, 1970; Sawicki, C. R., Anal. Lett., 4, pp.761–775, 1971; Damiani, P. and Burini, G., Talanta, 8, pp.649–652, 1986; Damiani, P. and Burini, G., Talanta, 8, pp.649–652, 1986; and Misko, T. P., Anal. Biochem.214, pp.11–16, 1993). For the nitrogen monoxide measurement according to the present invention, for example, irradiation with light of about 495 nm as excitation light, and measurement of fluorescence of about 515 nm may preferably be performed. By using the light having such wavelength, efficient cut off can be obtained by using a fluorescence filter provided on an ordinary fluorescence microscope, and measurement with high sensitivity can be achieved without using an unordinary filter.

Where particularly high sensitive measurement is required, the aforementioned measurement of nitrogen monoxide may be carried out in the presence of an oxygen source. As the oxygen source, for example, dioxygen, ozone, oxide compounds or other can be used. As the oxygen, dissolved dioxygen can generally be used, and if desired, dioxygen gas may be introduced into the reaction system or an agent that can generate dioxygen (e.g., hydrogen peroxide) may be added. The oxide compounds are not particularly limited so long as they have an oxide bond that can easily be cleaved, e.g., N—O, S—O, or P—O. For example, PTIO (2-phenyl-4,4,5,5-tetramethylimidazoline-1-oxyl-3-oxide Maeda, H., et al., J. Leuk. Biol., 56, pp.588–592, 1994; and Akaike, T., et al., Biochemistry, 32, pp.827–832, 1993) or derivatives thereof (carboxy-PTIO which has carboxyl group introduced at the para-position of the phenyl group of PTIO), triphenylphosphine oxide, triethylamine oxide or the like can be used.

Among the oxide compounds mentioned above, PTIO and derivatives thereof (e.g., carboxy-PTIO) are particularly preferred compounds, and they can be readily obtained by those skilled in the art (listed in, for example, Organic Chemicals Catalog, 32, 1994, Tokyo Kasei Co., Ltd.). The oxide compounds, per se, may be used as a reaction agent, or those encapsulated in liposomes or other may also be used. Although the amount of the oxygen source is not particularly limited, preferable amount may be at least 1 μmol or more, preferably 10–30 μmol, and more preferably about 10–20 µmol based on nitrogen monoxide to be measured. From 10 to 20 µmol of the oxide compound may preferably be added to samples for the measurement of the sample from a living body, however, a required amount of the oxygen source is generally supplied by dissolved dioxygen. If the amount of oxygen source is extremely small, measuring sensitivity may sometimes be lowered, and if an extremely large amount of oxygen source exist, emission of fluorescence may be disadvantageously affected. Therefore, it is preferred that an amount of nitrogen monoxide to be measured is predicted by a preliminary experiment or a known method so that the oxygen source within an appropriate concentration range can be applied. The reaction can be carried out at a temperature of from 10° to 25° C.

EXAMPLES

The present invention will be further explained more specifically by referring to the following examples. However, the scope of the present invention is not limited to these examples. In the examples, compound names such as "DAF-1" correspond to those mentioned in the scheme set out above.

Example 1

2,3-Dimethyl-6-nitroaniline was dissolved in acetic acid and acetylated with 1 equivalent of acetic anhydride to obtain 3-acetamide-4-nitroxylene. The resulting product was recrystallized from ethanol and then dissolved in hot water containing magnesium sulfate. To this solution, 6 equivalents of potassium permanganate suspended in water was added as several portions, and then the solution was refluxed by heating until purple color disappeared. The hot reaction mixture was filtered, and after cooling, the filtrate was acidified with hydrochloric acid and extracted with ethyl acetate. The resulting 3-acetamide-4-nitrophthalic acid was converted into acid anhydride using acetyl chloride in acetic anhydride. After evaporating the solvent under reduced pressure, a small amount of dry methylene chloride was added to the residue, and deposited solid was collected by filtration to obtain 3-acetamide-4-nitrophthalic acid anhydride. In a similar manner, 4-acetamide-5-nitrophthalic acid anhydride was prepared from 4,5-dimethyl-2-nitroaniline.

Example 2

Preparation of DAF-1

3-Acetamide-4-nitrophthalic acid anhydride and resorcinol were melted at 180° C., and after two hours, the mixture was added with zinc chloride and kept at 210° C. to dryness. After cooling, the resulting solid was refluxed in 0.6N hydrochloric acid for one hour. The reaction mixture was cooled and black solid was collected by filtration. The product was purified by silica gel column chromatography to obtain aminonitro-fluorescein. The resulting aminonitrofluorescein was reduced in water by using sodium sulfide and sodium hydrosulfide, and the product was purified by silica gel column chromatography to give the title compound.
3-Amino-4-nitrofluorescein (3-amino-4-nitro-3',6'-dihydroxy-spiro[isobenzofuran-1(3H), 9'-[9H]xanthen]-3-one) $C_{20}H_{12}N_2O_7$, F.W. 392.316 $^1$H-NMR (300 MHz, DMSO-$d_6$) δ 6.38 (d, 1H, J=8.6); 6.56 (dd, 2H, J=8.6, 2.4); 6.66 (d, 2H, J=2.4); 6.80 (d, 2H, J=8.6); 7.96 (s, 2H); 8.35 (d, 1H, J=8.6); 10.18 (s, 2H)
3,4-Diaminofluorescein (DAF-1: 4,5-diamino-3',6'-dihydroxy-spiro [isobenzofuran-1(3H), 9'-[9H]xanthen]-3-one) $C_{20}H_{14}N_2O_5$, F.W. 362.322, m.p. above 300° C., MS (EI) (m/z) M$^+$ 362 $^1$H-NMR (300 MHz, DMSO-$d_6$) δ 5.01 (s, 2H); 5.88 (s, 2H); 6.05 (d, 1H, J=7.5); 6.52 (dd, 2H, J=8.6, 2.4); 6.60 (d, 2H, J=2.4); 6.64 (d, 2H, J=8.6); 6.78 (d, 1H, J=7.5); 9.97 (s, 2H)

Example 3

Preparation of DAF-3

DAF-3 was produced in the same manner as in Example 2.
6-Amino-5-nitrofluorescein (6-amino-5-nitro-3',6'-dihydroxy-spiro [isobenzofuran-1(3H), 9'-[9H]xanthen]-3-one) $C_{20}H_{12}N_2O_7$, F.W. 392.316 $^1$H-NMR (300 MHz, DMSO-$d_6$) δ 6.40 (s, 2H); 6.56 (dd, 2H, J=8.6, 2.4); 6.71 (d, 2H, J=2.4); 6.72 (d, 2H, J=8.6); 7.22 (d, 1H, J=8.6); 8.38 (d, 1H, J=8.6); 10.18 (s, 2H)
5,6-Diaminofluorescein (DAF-3: 6,7-diamino-3',6'-dihydroxy-spiro[isobenzofuran-1(3H), 9'-[9H]xanthen]-3-one) $C_{20}H_{14}N_2O_5$, F.W. 362.322, m.p. 220°–230° C., MS (EI) (m/z) M$^+$ 362 $^1$H-NMR (300 MHz, DMSO-$d_6$) δ 3.80 (s, 2H); 5.58 (s, 2H); 6.53 (dd, 2H, J=8.6, 2.4); 6.62 (d, 2H, J=8.6); 6.65 (d, 2H, J=2.4); 6.79 (d, 1H, J=7.9); 7.07 (d, 1H, J=7.9); 10.01 (s, 2H)

Example 4

Preparation of DAF-2

In the same manner as in Example 2, DAF-2 was prepared by using 4-acetamide-5-nitrophthalic acid anhydride and resorcinol.
5-Amino-4-nitrofluorescein (5-amino-4-nitro-3',6'-dihydroxy-spiro[isobenzofuran-1(3H), 9'-[9H]xanthen]-3-one) $C_{20}H_{12}N_2O_7$, F.W. 392.316 $^1$H-NMR (300 MHz, DMSO-$d_6$) δ 6.58 (dd, 2H, J=8.6, 2.2); 6.63 (s, 1H); 6.65 (d, 2H, J=2.2); 6.75 (d, 2H, J=8.6); 7.92 (s, 2H); 8.49 (s, 1H); 10.17 (s, 2H)
4-Amino-5-nitrofluorescein (4-amino-5-nitro-3',6'-dihydroxy-spiro[isobenzofuran-1(3H), 9'-[9H]xanthen]-3-one) $C_{20}H_{12}N_2O_7$, F.W. 392.316 $^1$H-NMR (300MHz, DMSO-$d_6$) δ 6.55 (dd, 2H, J=8.6, 2.2); 6.65 (d, 2H, J=2.2); 6.74 (d, 2H, J=8.6); 7.59 (s, 1H); 7.73 (s, 2H); 7.74 (s, 1H); 10.12 (s, 2H)
4,5-Diaminofluorescein (DAF-2: 5,6-diamino-3',6'-dihydroxy-spiro[isobenzofuran-1(3H), 9'-[9H]xanthen]-3-one) $C_{20}H_{14}N_2O_5$, F.W. 362.322, m.p. 240°–250° C., MS (EI) (m/z) M$^+$ 362 $^1$H-NMR (300 MHz, DMSO-$d_6$) δ 5.00 (s, 2H); 5.58 (s, 2H); 6.07 (s, 1H); 6.52 (dd, 2H, J=8.6, 2.2); 6.60 (d, 2H, J=2.2); 6.60 (d, 2H, J=8.6); 6.89 (s, 1H); 9.99 (s, 2H)

Example 5

Preparation of DAF-4 and DAF-6

In the same manner as in Example 2, DAF-4 and DAF-6 were produced by using 3-acetamide-4-nitrophthalic acid anhydride and 4-chlororesorcinol.
3-Amino-4-nitrodichlorofluorescein (3-amino-4-nitro-2',7'-dichloro-3',6'-dihydroxy-spiro-[isobenzofuran-1(3H),9'-[9H]xanthen]-3-one) $C_{20}H_{10}Cl_2N_2O_7$, F.W. 461.200 $^1$H-NNMR (300 MHz, DMSO-$d_6$) δ 6.41 (d, 1H, J=8.6); 6.87 (s, 2H); 7.03 (s, 2H); 7.83 (s, 2H); 8.36 (d, 1H, J=8.6); 11.23 (s, 2H)
3,4-Diaminodichlorofluorescein (DAF-4: 4,5-diamino-2',7'-dichloro-3',6'-dihydroxy-spiro- [isobenzofuran-1(3H),9'-[9H]xanthen]-3-one) $C_{20}H_{12}Cl_2N_2O_5$, F.W. 431.216, m.p. sublimated at above 240° C. and did not melt at 300° C. MS (EI) (m/z) M$^+$ 430 $^1$H-NMR (300 MHz, DMSO-d$_6$) δ 5.14 (s, 2H); 5.97 (s, 2H); 6.12 (d, 1H, J=7.7); 6.68 (s, 2H, 6.81 (d, 1H, J=7.7); 6.85 (s, 2H); 10.97 (s, 2H)

6-Amino-5-nitrodichlorofluorescein (6-amino-5-nitro-2',7'-dichloro-3',6'-dihydroxy-spiro-[isobenzofuran-1(3H),9'-[9H]xanthen]-3-one) $C_{20}H_{10}Cl_2N_2O_7$, F.W. 461.200 $^1$H-NMR (300 MHz, DMSO-d$_6$) δ 6.60 (s, 2H); 6.93 (s, 2H); 6.93 (s, 2H); 7.22 (d, 1H, J=8.6); 8.40 (d, 1H, J=8.6); 11.17 (s, 2H)

5,6-Diaminodichlorofluorescein (DAF-6: 6,7-diamino-2',7'-dichloro-3',6'-dihydroxy-spiro-[isobenzofuran-1(3H),9'-[9H]xanthen]3-one) $C_{20}H_{12}Cl_2N_2O_5$, F.W. 431.216, m.p. 190°–215° C., MS (EI) (m/z) M$^+$ 430 $^1$H-NMR (300 MHz, DMSO-d$_6$) δ 4.06 (s, 2H); 5.74 (s, 2H); 6.61 (s, 2H); 6.84 (d, 1H, J=7.9); 6.89 (s, 2H); 7.10 (d, 1H, J=7.9); 10.97 (s, 2H)

Example 6

Preparation of DAF-5

In the same manner as in Example 2, DAF-5 was prepared by using 4-acetamide-5-nitrophthalic acid anhydride and 4-chlororesorcinol.

5-Amino-4-nitrodichlorofluorescein (5-amino-4-nitro-2',7'-dichloro-3',6'-dihydroxy-spiro-[isobenzofuran-1(3H),9'-[9H]xanthen]-3-one) $C_{20}H_{10}Cl_2N_2O_7$, F.W. 461.200 $^1$H-NMR (300 MHz, DMSO-d$_6$) δ 6.66 (s, 1H); 6.89 (s, 2H); 6.91 (s, 2H); 7.96 (s, 2H) 8.48 (s, 1H); 11.11 (s, 2H)

4-Amino-5-nitrodichlorofluorescein (4-amino-5-nitro-2',7'-dichloro-3',6'-dihydroxy-spiro-[isobenzofuran-1(3H),9'-[9H]xanthen]-3-one) $C_{20}H_{10}Cl_2N_2O_7$, F.W. 461.200 $^1$H-NMR (300 MHz, DMSO-d$_6$) δ 6.9 (br, 2H); 6.91 (s, 2H); 7.63 (s, 1H); 7.77 (s, 2H); 7.86 (s, 1H); 11.07 (s, 2H)

4,5-Diaminodichlorofluorescein (DAF-5: 5,6-diamino-2',7'-dichloro-3',6'-dihydroxy-spiro-[isobenzofuran-1(3H),9'-[9H]xanthen]-3-one) $C_{20}H_{12}Cl_2N_2O_5$, F.W. 431.216, m.p. 215°–220° C., MS (EI) (m/z) M$^+$ 430 $^1$H-NMR (300 MHz, DMSO-d$_6$) δ 5.12 (s, 2H); 5.69 (s, 2H); 6.12 (s, 1H); 6.63 (s, 2H) 6.85 (s, 2H); 6.93 (s, 1H); 10.96 (s, 2H)

Example 7

Preparation of DAF-2 DA

DAF-2 obtained in Example 4 was dissolved in acetonitrile containing cesium carbonate, and the solution was added with 1 equivalent of acetic anhydride and stirred at room temperature for one hour. After evaporating the solvent under reduced pressure, the residue was purified by silica gel column chromatography to obtain DAF-2 DA.

4,5-Diaminofluorescein diacetate (DAF-2 DA: 5,6-diamino-3',6'-bis(acetyloxy)-spiro[isobenzofuran-1(3H),9'- [9H]xanthen]- 3-one) $C_{24}H_{18}N_2O_7$, F.W. 446.404, m.p. 110°–120° C., MS (EI) (m/z) M$^+$ 446 $^1$H-NMR (300 MHz, Acetone-d$_6$) δ 2.27 (s, 6H); 4.68 (s, 2H); 5.16 (s, 2H); 6.34 (s, 1H); 6.92 (dd, 2H, J=8.6, 2.2); 7.00 (d, 2H, J=8.6); 7.12 (d, 2H, J=2.2); 7.15 (s, 1H)

Elemental analysis: C, 64.57; H, 4.06; N 6.28. Found: C, 64.27; H, 4.16; N 6.18.

Example 8

Preparation of triazole compound

Fluorescein compounds obtained in Examples 2–7 were each dissolved in methanol, and bubbled with nitrogen monoxide gas, and the solvent was evaporated under reduced pressure. The residue was purified by silica gel column chromatography to afford corresponding triazole compounds.

3,4-Fluoresceintriazole (DAF-1T: 3",6"-dihydroxy-spiro[ [4',5':4,5]triazoloisobenzo-furan-1(3H),9"-[9H]xanthen]-3-one) $C_{20}H_{11}N_3O_5$, F.W. 373.318, m.p. above 300° C., MS (EI) (m/z) M$^+$ 373 $^1$H-NMR (300 MHz, Acetone-d$_6$) δ 6.60 (dd, 2H, J=8.6, 2.4); 6.77 (d, 2H, J=2.4); 6.77 (d, 2H, J=8.6); 7.23 (d, 1H, J=7.7); 8.43 (d, 1H, J=7.7); 9.05 (s, 2H) Peak wavelengths: Ex. 493 nm - Em. 521 nm 4,5-Fluoresceintriazole (DAF-2T: 3",6"-dihydroxy-spiro[ [4',5':5,6]triazoloisobenzo-furan-1(3H), 9"-[9H]xanthen]-3-one) $C_{20}H_{11}N_3O_5$, F.W. 373.318, m.p. above 300° C., MS (EI) (m/z) M$^+$ 373 $^1$H-NMR (300 MHz, Acetone-d$_6$) δ 6.59 (dd, 2H=8.8, 2.4); 6.72 (d, 2H, J=8.8);6.75 (d, 2H, J=2.4); 7.68 (s, 1H); 8.56 (s, 1H) Peak wavelengths: Ex. 491 nm - Em. 513 nm 5,6-Fluoresceintriazole (DAF-3T: 3",6"-dihydroxy-spiro[ [4',5':6,7]triazoloisobenzo-furan-1(3H),9"-[9H]xanthen]-3-one) $C_{20}H_{11}N_3O_5$, F.W. 373.318, m.p. above 300° C., MS (EI) (m/z) M$^+$ 373 $^1$H-NMR (300 MHz, Acetone-d$_6$) δ 6.54 (dd, 2H, J=8.6, 2.4); 6.67 (d, 2H, J=8.6); 6.79 (d, 2H, J=2.4); 8.00 (d, 1H, J=8.0); 8.24 (d, 1H, J=8.0); 9.00 (s, 2H) Peak wavelengths: Ex. 494 nm - Em. 521 nm 3,4-Dichlorofluoresceintriazole (DAF-4T: 3",6"-dihydroxy-2",7"-dichloro-spiro-[[4',5':4,5]-triazoloisobenzofuran-1 (3H),9"-[9H]xanthen]-3-one $C_{20}H_9Cl_2N_3O_5$, F.W. 442.202, m.p. above 300° C. MS (EI) (m/z) M$^+$ 441 $^1$H-NMR (300 MHz, Acetone-d$_6$) δ 6.97 (s, 2H); 7.00 (s, 2H); 7.31 (d, 1H, J=9.0); 8.46 (d, 1H, J=9.0); 9.70 (s, 2H) Peak wavelengths: Ex. 505 nm - Em. 530 nm 4,5-Dichlorofluoresceintriazole (DAF-5T: 3",6"-dihydroxy-2",7"-dichloro-spiro-[[4',5':5,6]-triazoloisobenzofuran-1 (3H),9"-[9H]xanthen]-3-one) $C_{20}H_9Cl_2N_3O_5$, F.W. 442.202, m.p. above 300° C., MS (EI) (m/z) M$^+$ 441 $^1$H-NMR (300 MHz, Acetone-d$_6$) δ 6.86 (s, 2H); 6.93 (s, 2H); 7.8 (br, 1H); 8.6(br, 1H); 9.62 (s, 2H) Peak wavelengths: Ex. 503 nm - Em. 523 nm 5,6-Dichlorofluoresceintriazole (DAF-6T: 3",6"-dihydroxy-2",7"-dichloro-spiro-[[4',5':6,7]-triazoloisobenzofuran-1 (3H),9"-[9H]xanthen]-3-one) $C_{20}H_9Cl_2N_3O_5$, F.W. 442.202, m.p. above 300° C., MS (EI) (m/z) M$^+$ 441 $^1$H-NMR (300 MHz, Acetone-d$_6$) δ 6.88 (s, 2H); 7.00 (s, 2H); 8.04 (d, 1H, J=8.0); 8.23 (d, 1H, J=8.0); 9.68 (s, 2H) Peak wavelengths: Ex. 506 nm - Em. 529 nm Example 9

Figure 1A:
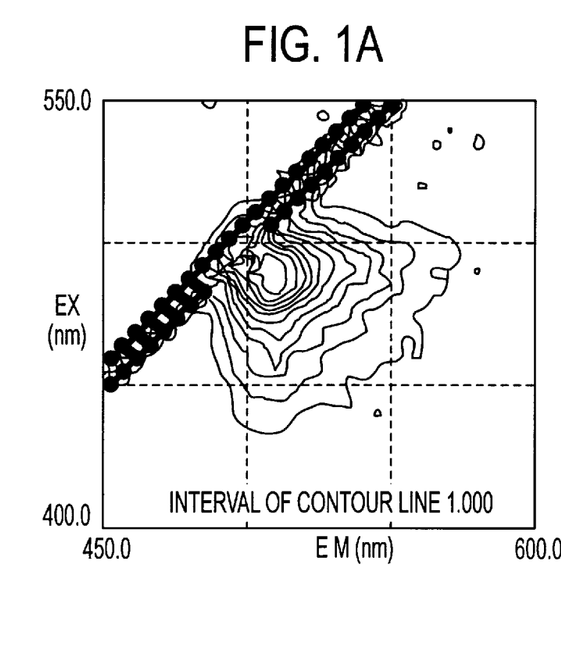
FIG. 1 shows changes of fluorescence spectrum of a compound of the formula (I) after the addition of nitrogen monoxide. FIG. (a) shows fluorescence spectrum of the compound of the formula (I) before introducing a gas, and FIG. (b) shows fluorescence spectrum of the compound of the formula (II) formed in a reaction system after introducing the gas.
Figure 1B:
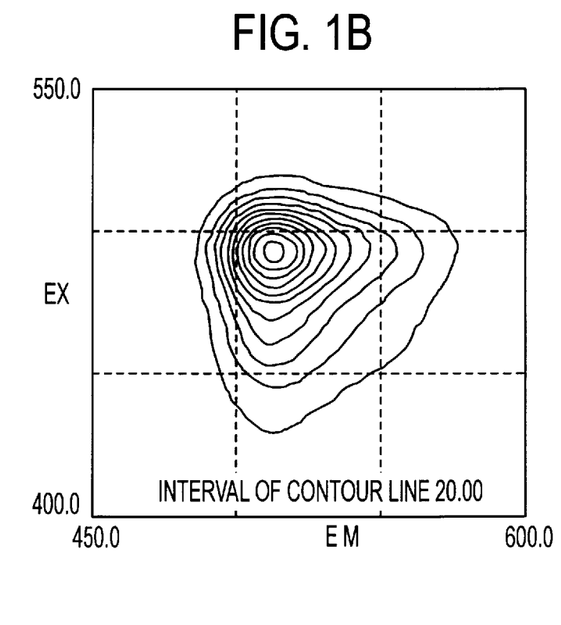

Changes of Fluorescence Spectrum of the Compound of the Formula (I) by Addition of Nitrogen Monoxide DAF-2 was dissolved at 1 μM in 0.1M phosphate buffer (pH 7.4), and changes of fluorescence spectrums were measured before and after the solution was bubbled with nitrogen monoxide gas. The results are shown in FIG. 1. In the FIG. (a) shows the fluorescence spectrum before introducing the gas, and (b) shows the spectrum after introducing the gas. Intensities at maximum fluorescence wavelengths before and after the gas introduction were 12.24 (Ex. 495 nm-Em. 505 nm) and 232.9 (Ex. 495 nm-Em. 515 nm), respectively. There was an approximately 19-fold increase of intensity at maximum fluorescence wavelength because of the triazole compound (DAF-2T) formed in the reaction system after the gas introduction.

Example 10

Changes of Fluorescence Intensity of the Compound of the Formula (I) Depending on the Amount of Generated Nitrogen Monoxide As a nitrogen monoxide source, among NOCs, i.e., the spontaneous NO generating agents (Hrabie, J. A., J. Org.

Figure 2A:
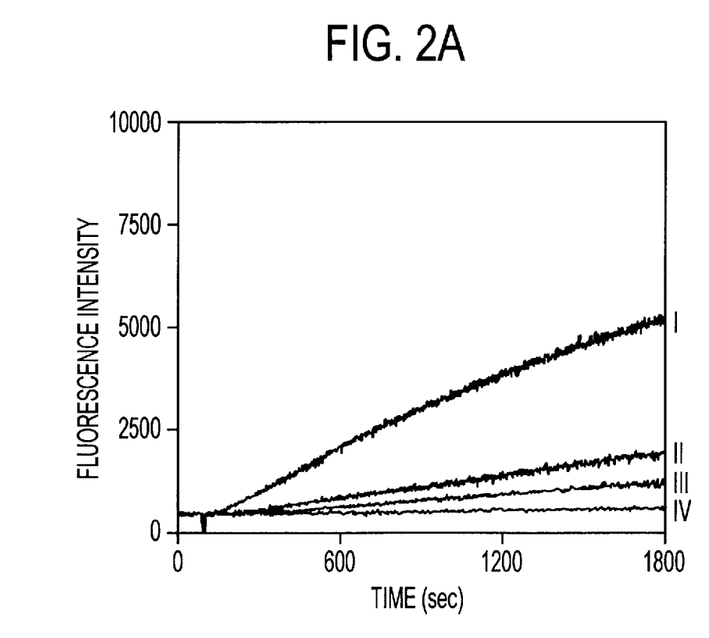
FIG. 2 shows changes of fluorescence intensity of a compound of the formula (I) depending on the amount of generated nitrogen monoxide. In this FIG. (a) and (b) show the results obtained by using NOC12 and NOC13, respectively, and I, II, III, and IV, and I', II', and IV' represent the results obtained in the presence of NOCs at 500 μM, 100 μM, 50 μM, and 5, μM, respectively.
Figure 2B:
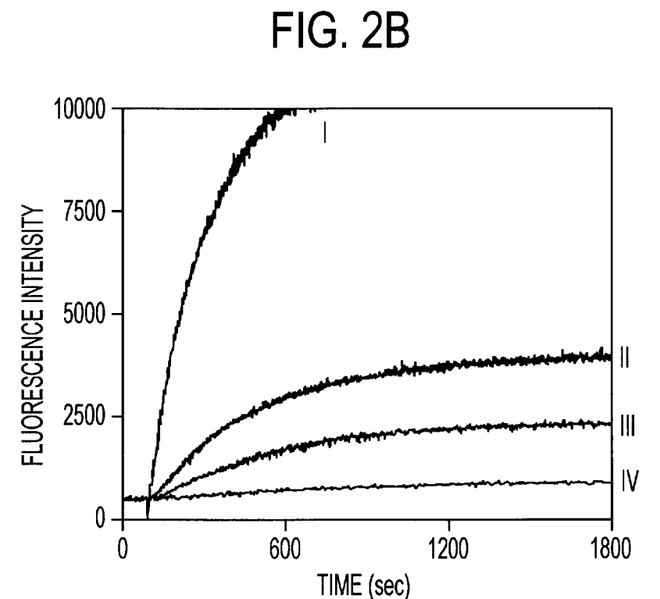

Chem., 58, pp.1472–1476, 1993), NOC-12 (half life in 0.1M phosphate buffer, pH 7.4, at 22° C.: 327 minutes) and NOC-13 (half life: 13.7 minutes) were used. The nitrogen monoxide formed in the reaction mixture was allowed to react with DAF-2. As a reaction solvent, 0.1M phosphate buffer (pH 7.4) was used, and 10 $\mu$M of DAF-2 was subjected to the reaction in the presence of various concentrations of the NOCs (5 $\mu$M, 50 $\mu$M, 100 $\mu$M, and 500 $\mu$M) at 37° C. and changes of fluorescence intensity were measured (measuring wavelength: Ex. 495 nm-Em. 515 nm). The results are shown in FIG. 2. In the FIG. (a) and (b) show the results obtained by using NOC12 and NOC13, respectively, and I, II, III, and IV, and I', II', III', and IV' represent the results obtained at the concentrations of 500 $\mu$M, 100 $\mu$M, 50 $\mu$M, and 5 $\mu$M of NOCs, respectively. From these results, it is clearly demonstrated that triazole compounds were formed from DAF-2 depending on the amount of generated nitrogen monoxide, and that changes of fluorescence intensity precisely reflecting the nitrogen monoxide concentration can be observed.

Example 11

Sensitivity of the Measurement of Nitrogen Monoxide Using the Compound of the Formula (I)

DAF-2 was used as the compound of formula (I), and sensitivity of measurement of nitrogen monoxide was compared with that obtained by using 2,3-diaminonaphthalene. DAF-2 (10 $\mu$M) and 2,3-diaminonaphthalene (100 $\mu$M) were separately dissolved in 0.1M phosphate buffer (pH 7.4) at 37° C. The solutions were added with a nitrogen monoxide solution, and then increased fluorescence intensities due to the changes of nitrogen monoxide concentration were measured. The nitrogen monoxide solution was prepared by substituting 0.1M phosphate buffer (pH 7.4) with argon gas, followed by bubbling nitrogen monoxide into the solution. Concentrations were determined by the HRP method (Kikuchi, K. et al., Biol. Pharm. Bull., 19, pp.649–651, 1996). Wavelengths for fluorescence measurements were Ex. 495 nm, Em. 515 nm for DAF-2; and Ex.375 nm, Em. 425 nm for 2,3-diaminonaphthalene. The results obtained by comparing sensitivities based on a calibration curve were shown in FIG. 3($a$). In this figure, □ represents the results obtained by DAF-2, and ○ represents the results obtained by 2,3-diaminonaphthalene. From these results, it is clearly demonstrated that DAF-2 has approximately 5 times higher sensitivity compared to 2,3-diaminonaphthalene.

Figure 3A:
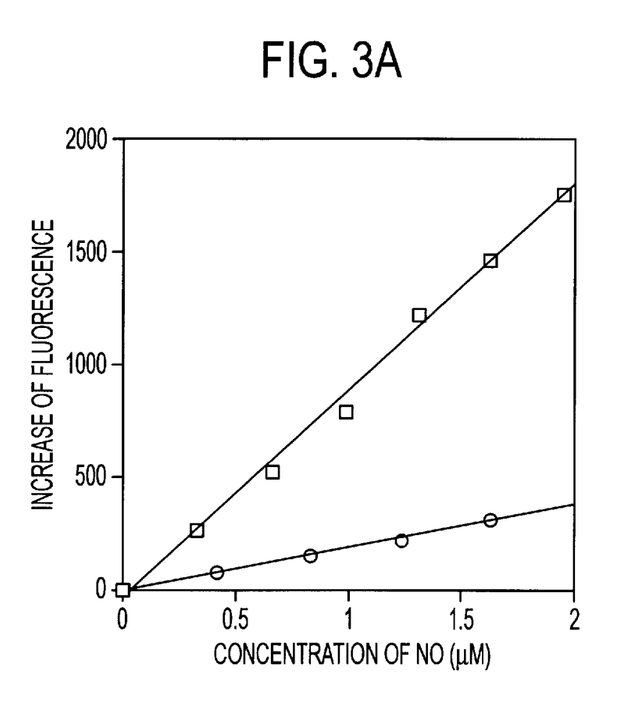
FIG. 3 shows results of comparison of sensitivity between a compound of the formula (I) and 2,3-diaminonaphthalene. In this FIG. (a) shows the results of comparison of sensitivity using a calibration curve, and □ represents the results obtained by using DAF-2 and ○ represents the results obtained by using 2,3-diaminonaphthalene. FIG. (b) represents fluorescence intensity of triazole compounds formed by the reaction with nitrogen monoxide, and in the figure, □ represents the results obtained by using DAF-2 and ○ represents the results obtained by using naphthotriazole.
Figure 3B:
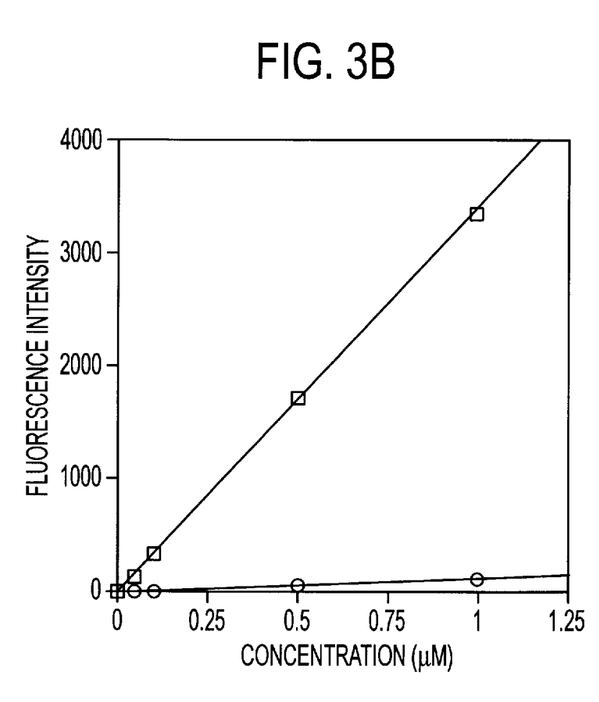

Synthesized authentic samples of triazole compounds formed by respective reactions of DAF-2 and 2,3-diaminonaphthalene with nitrogen monoxide were dissolved in 0.1M phosphate buffer (pH 7.4), and increases of fluorescence intensity depending on the increased concentrations were measured. Wavelengths of fluorescence measurement were Ex.495 nm, Em.515 nm for the triazole compound derived from DAF-2 (DAF-2T); and Ex. 375 nm, Em.425 nm for the triazole compound derived from 2,3-diaminonaphthalene (naphthotriazole). The results are shown in FIG. 3($b$). In the figure, □ represents the results obtained by DAF-2, and ○ represents the results obtained by naphthotriazole. From these results, it is clearly revealed that the triazole compound derived from DAF-2 has about 24 times higher sensitivity compared to naphthotriazole.

Example 12

Changes of Sensitivity by pH Fluctuation

Figure 4:
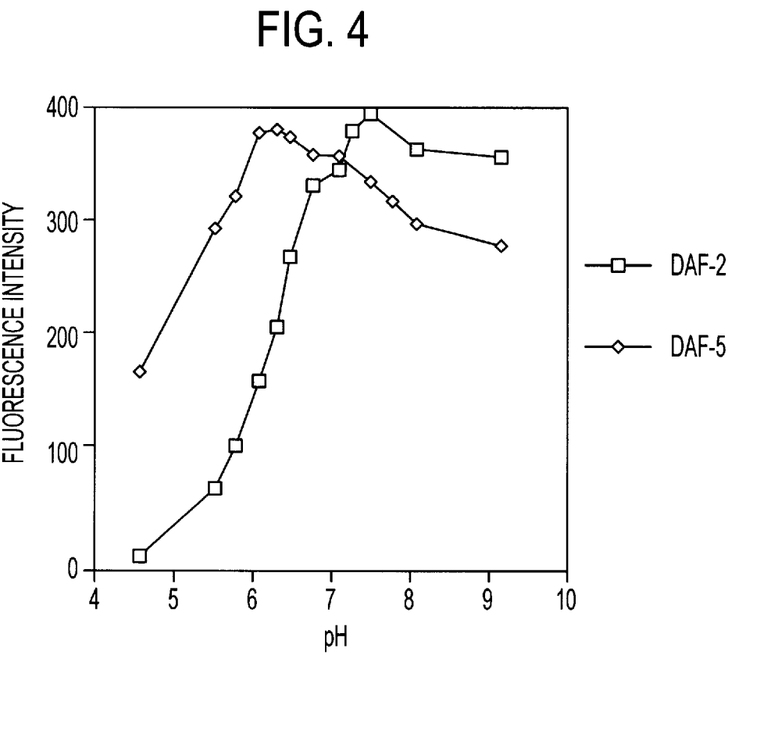
FIG. 4 shows changes of sensitivity of the compound of the formula (I) due to pH fluctuation. In this figure, □ represents the results obtained by using DAF-2 and ◇ represents the results obtained by using DAF-5.
Figure 5A:
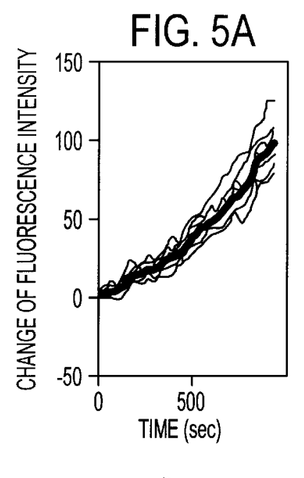
FIG. 5 shows results of measurement of nitrogen monoxide existing in individual cells. In the FIG. (a), (b), and (c)
Figure 5B:
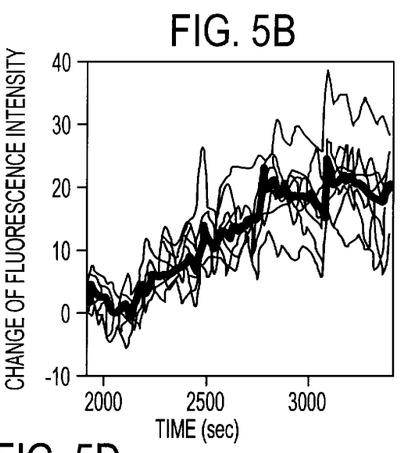
Figure 5C:
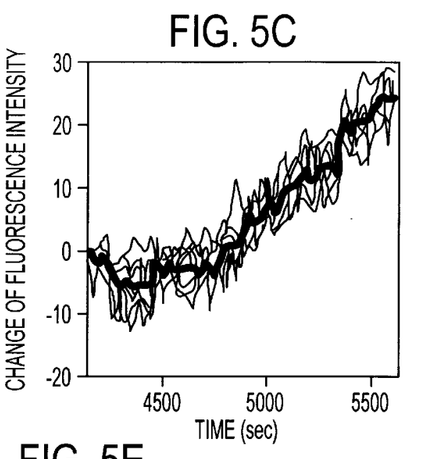
Figure 5D:
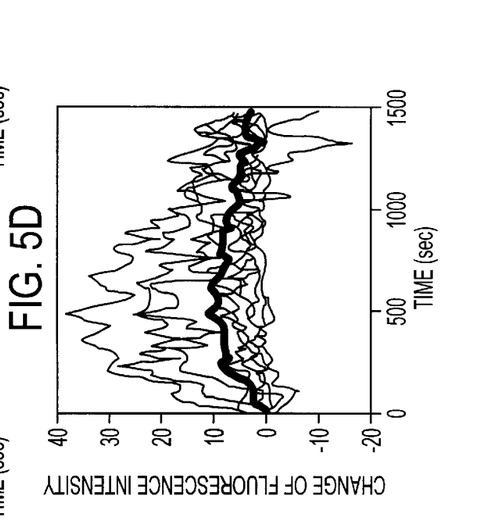
Figure 5E:
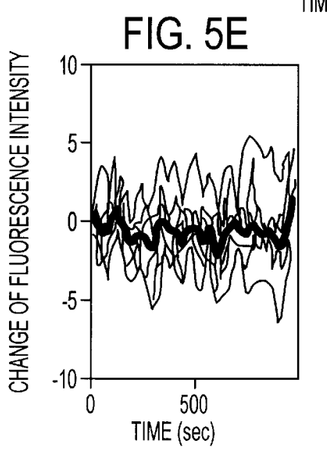

DAF-2 and DAF-5 were used as the compounds of formula (I), and they were separately dissolved in 0.1M phosphate buffer (pH 7.4) at a concentration of 100 $\mu$M and then the solutions were bubbled with nitrogen monoxide. Each of the solutions was added to phosphate buffers having different pHs at a final concentration of about 1 $\mu$M, and then fluorescence intensities were measured. Wavelengths of fluorescence measurement were Ex.495 nm, Em.515 nm for DAF-2; and Ex. 505 nm, Em.520 nm for DAF-5. The results are shown in FIG. 4. In the figure, □ represents the results obtained by DAF-2, and ◇ represents the results obtained by DAF-5. From these results, it is apparent that DAF-2 maintains high sensitivities under neutral to mildly alkaline region, and DAF-5 maintains high sensitivity in the wide range of pH, i.e., ranging from weakly acidic to mildly alkaline condition.

Example 13

Imaging of Nitrogen Monoxide Produced by Vascular Smooth Muscle Cells

Vascular smooth muscle cells derived from rat aorta were cultured in a glass-bottom dish, and nitrogen monoxide synthetase was induced by stimulation with LPS (12.5 $\mu$g/ml), IFN-$\gamma$ (150 U/ml), IL-1$\beta$ (25 U/ml), and TNF-$\alpha$ (30 ng/ml). The cultivation was continued for about 12 hours, and the medium was changed to Krebs-Ringer-phosphate buffer (KRP) containing dissolved DAF-2 DA (Example 7, 10 $\mu$M) to allow the DAF-2 DA become intracellularly taken. After cultivation at 37° C. for one hour, the cells were washed and the medium was changed to Krebs-Ringer-phosphate buffer (KRP) containing dissolved L-Arg or L-NMMA. Changes of fluorescence intensity in the cells with time were measured by using a fluorescence microscopy (Ex.490, Em.not shorter than 515 nm; magnification ×20).

The results are shown in FIG. 5. In the FIG. (a), (b), and (c) show the results obtained by successive experiments. FIG. (a) shows the fluorescent changes after the culture medium of the stimulated cells was replaced with a culture medium containing 1 mM L-Arg; FIG. (b) shows the changes after the culture medium of the step (a) was replaced with a culture medium containing 1 mM NMMA; and FIG. (c) shows the changes after the culture medium of the step (b) was replaced with a culture medium containing 10 mM L-Arg. FIG. (d) shows the changes after the culture medium of the stimulated cells was replaced with a culture medium containing 1 mM NMMA. FIG. (e) shows the changes after the culture medium of the non-stimulated cells was replaced with a culture medium containing 1 mM L-Arg. The normal lines represent fluorescence intensities of individual cells, and the bold lines represent average values. From these results, DAF-2 DA was revealed to react with nitrogen monoxide in the cells and emit fluorescence after having been taken into the cells.

From the foregoing explanation, it can be understood that the compounds of the present invention are useful as reagents for measuring nitrogen monoxide. The compounds of formula (I) of the present invention can efficiently react with nitrogen monoxide to give fluorescent compounds according to the formula (II). The compounds of the formula (II) emit strong fluorescence when irradiated with excitation light having a long wavelength that does not damage living tissues and cells, and they are characterized be used for accurate measurement of intracellular nitrogen monoxide concentration of individual cells.

What is claimed is:

1. A compound represented by the following formula (I):

wherein $R^1$ and $R^2$ represent amino groups that substitute at adjacent positions on the phenyl ring; $R^3$ and $R^4$ independently represent a hydrogen atom or an acyl group; $R^5$, $R^6$, $R^7$, and $R^8$ independently represent a hydrogen atom, a $C_{1-6}$ alkyl group, allyl group, or a halogen atom.

2. The compound according to claim 1 wherein $R^3$ and $R^4$ independently represent a hydrogen atom or a $C_{1-6}$ alkylcarbonyl group; and $R^5$, $R^6$, $R^7$, and $R^8$ independently represents a hydrogen atom or a chlorine atom.

3. A reagent for measurement of nitrogen monoxide which comprises the compound according to claim 1.

4. A compound represented by the following formula (II):

wherein $R^{11}$ and $R^{12}$ combine together to form a group represented by —N=N—NR$^{19}$— which forms a ring structure at adjacent positions on the phenyl ring wherein $R^{19}$ represents a hydrogen atom, a $C_{1-18}$ alkyl group, or a substituted or unsubstituted aralkyl group, or $R^{11}$ and $R^{12}$ represents a combination of an amino group and a nitro group which substitute at adjacent positions on the phenyl ring; $R^{13}$ and $R^{14}$ independently represent a hydrogen atom or an acyl group; and $R^{15}$, $R^{16}$, $R^{17}$, and $R^{18}$ independently represent a hydrogen atom, a $C_{1-6}$ alkyl group, allyl group, or a halogen atom.

5. The compound according to claim 4 wherein $R^{13}$ and $R^{14}$ independently represents a hydrogen atom or a $C_{1-6}$ alkylcarbonyl group; and $R^{15}$, $R^{16}$, $R^{17}$, and $R^{18}$ independently represent a hydrogen atom or a chlorine atom.

6. A method for measuring nitrogen monoxide which comprises the steps of:

(1) reacting a compound represented by the following formula (I):

wherein $R^1$ and $R^2$ represent amino groups that substitute at adjacent positions on the phenyl ring; $R^3$ and $R^4$ independently represent a hydrogen atom or an acyl group; $R^5$, $R^6$, $R^7$, and $R^8$ independently represent a hydrogen atom, a $C_{1-6}$ alkyl group, allyl group, or a halogen atom; and (2) detecting a compound of the formula (II):

wherein $R^{11}$ and $R^{12}$ combine together to form a group represented by —N=N—NR$^{19}$— which forms a ring structure at adjacent positions on the phenyl ring wherein $R^{19}$ represents a hydrogen atom, a $C_{1-18}$ alkyl group, or a substituted or unsubstituted aralkyl group; $R^{13}$ and $R^{14}$ independently represent a hydrogen atom or an acyl group; and $R^{15}$, $R^{16}$, $R^{17}$, and $R^{18}$ independently represent a hydrogen atom, a $C_{1-6}$ alkyl group, allyl group, or a halogen atom.

7. The method according to claim 6, wherein the measurement is carried out under substantially a neutral condition.

8. The method according to claim 6, wherein the measurement is carried out by using an excitation light having a wavelength of about 495 nm.

9. The method according to claim 6, wherein the method is carried out for measuring intracellular nitrogen monoxide concentration of an individual cell.

10. The method according to claim 6, wherein the measurement is carried out in the presence of an oxygen source.

11. The method according to claim 10, wherein the oxygen source is PTIO.

* * * * *